United States Patent [19]

Sanders et al.

[11] Patent Number: 5,482,979
[45] Date of Patent: Jan. 9, 1996

[54] COMPOUNDS CONTAINING TERTIARY AMINO GROUPS, A PROCESS FOR THEIR PRODUCTION AND THEIR USE AS CATALYSTS

[75] Inventors: Josef Sanders, Leverkusen; Ulrich Liman, Langenfeld; Klaus König, Odenthal, all of Germany

[73] Assignee: Bayer Aktiengesellschaft, Leverkusen, Germany

[21] Appl. No.: 255,524

[22] Filed: Jun. 8, 1994

[30] Foreign Application Priority Data

Jun. 16, 1993 [DE] Germany ............................ 43 19 948.8

[51] Int. Cl.$^6$ ....................... C08G 18/18; C07C 229/02
[52] U.S. Cl. ....................... 521/129; 264/45.1; 264/45.2; 264/46.4; 521/128; 521/130; 521/155; 560/155; 560/156; 560/169; 560/295
[58] Field of Search ..................... 560/155, 156, 560/169, 205; 528/75, 85, 229; 521/128, 129, 155, 130; 264/45.1, 45.2, 46.4

[56] References Cited

U.S. PATENT DOCUMENTS

| 3,666,729 | 5/1972 | Ritchie et al. | |
| 3,691,112 | 9/1972 | Grogler et al. | |
| 5,159,048 | 10/1992 | Cassidy et al. | 528/53 |
| 5,200,434 | 6/1993 | Bailey, Jr. et al. | 521/129 |
| 5,229,430 | 7/1993 | Tamano et al. | 521/129 |
| 5,315,041 | 5/1994 | Abe et aL. | 521/129 |
| 5,374,666 | 12/1994 | Tamano et al. | 571/129 |

OTHER PUBLICATIONS

CA: 88:153,430 Dec. 1977.

*Primary Examiner*—James J. Seidleck
*Assistant Examiner*—John M. Cooney, Jr.
*Attorney, Agent, or Firm*—Joseph C. Gil; Lyndanne M. Whalen

[57] ABSTRACT

Compounds containing ester groups and tertiary amino groups and optionally hydroxyl groups are made by reacting optionally hydroxyfunctional acetoacetic acid esters of monofunctional or polyfunctional alcohols (particularly polyfunctional polyether polyols) with primary/tertiary polyamines (particularly diamines). These compounds are useful as optionally incorporable catalysts for the isocyanate addition reaction in the production of polyurethane foams by the isocyanate polyaddition process.

6 Claims, No Drawings

COMPOUNDS CONTAINING TERTIARY AMINO GROUPS, A PROCESS FOR THEIR PRODUCTION AND THEIR USE AS CATALYSTS

BACKGROUND OF THE INVENTION

This invention relates to new aminocrotonic acid esters containing tertiary amino groups, to a process for their production and to their use as catalysts or activators in the production of polyurethane foams.

The production of aminocrotonic acid esters by reaction of acetoacetic acid esters of monohydric or polyhydric alcohols (particularly polyether polyols of relatively high molecular weight) with ammonia, amines or aminoalcohols has been disclosed in the prior art. For example, DE-A-1,935,484 describes the reaction of acetoacetic acid esters with ammonia or monoamines. DE-A-1,935,485 and EP-A 0,429,169 describe the production of aminocrotonic acid esters by reaction of the acetoacetic acid esters mentioned with diamines or aminoalcohols. The products of these disclosed processes are modified polyols which are terminated by alcoholic hydroxyl groups or primary or secondary amino groups. Thee products are of interest as reactants for organic polyisocyanates in the production of polyurethanes or polyureas by the isocyanate polyaddition process.

SUMMARY OF THE INVENTION

It is an object of the present invention to provide new aminocrotonic acid esters containing tertiary amino groups.

It is also an object of the present invention to provide a process for the production of these new aminocrotonic acid esters containing tertiary amino groups.

It is another object of the present invention to provide new catalysts which are useful in the production of polyurethanes.

These and other objects which will be apparent to those skilled in the art are accomplished by reacting compounds corresponding to Formula II

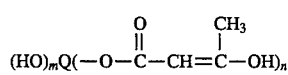

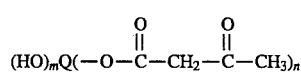

with compounds corresponding to Formula III

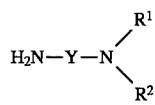

to form the aminocrotonic acid esters containing tertiary amino groups corresponding to Formula I

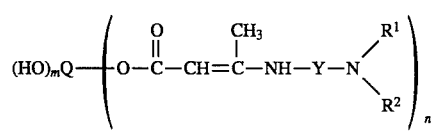

in which

Q, Y, $R^1$, $R^2$, m, and n represent the groups or values specified below.

DETAILED DESCRIPTION OF THE PRESENT INVENTION

It has now surprisingly been found that aminocrotonic acid esters terminated by tertiary amino groups corresponding to Formula I are particularly valuable catalysts for the isocyanate polyaddition process. catalysts are capable of being incorporated if hydroxyl groups are simultaneously present.

The compounds of the present invention may be used with particular advantage as catalysts for the production of composite materials by the backfoaming of plastic films which are used to a relatively large extent, for example in the production of upholstered furniture. It has often been found that the catalysts used in such processes (for example, low molecular weight tertiary amines such as triethylenediamine (commercially available under the name Dabco) or triethylamine) diffuse into the covering materials and damage them, particularly under the effect of sunlight and heat. In addition, these known catalysts enter the environment and contribute to so-called fogging, in many cases with odor emission. The use of organotin compounds generally leads to an improvement in ageing behavior. However, organotin catalysts present problems because of their susceptibility to hydrolysis in water-containing polyol systems so that a constant activation of such polyol components over prolonged periods of storage is not possible.

It has been found that the problems encountered with known catalysts mentioned above can be optimally solved by using the compounds corresponding to Formula I as catalysts.

The present invention relates to compounds containing tertiary amino groups which correspond to Formula (I) below:

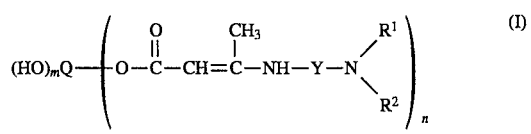

in which

Q is the residue obtained by removal of the hydroxyl group(s) from an (m+n)-functional alcohol having a molecular weight of from about 32 to about 6,000, Y is a difunctional aliphatic hydrocarbon radical containing from 2 to 6 carbon atoms with at least two carbon atoms being arranged between-the two nitrogen atoms, $R^1$ and $R^2$ which may be the same or different each represents an alkyl radical which may also be attached together with the nitrogen atom and, optionally, other hetero atoms and alkyl-substituted hetero atoms to form a saturated heterocyclic ring, m represents a number of from 0 to 7 and n represents a number of from 1 to 8, with the proviso that the sum m+n is a number of from 1 to 8.

The present invention also relates to a process for the production of compounds corresponding to Formula (I) in which compounds corresponding to Formula (II):

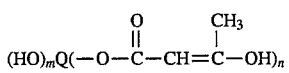
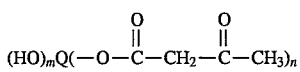

are reacted with compounds corresponding to Formula (III):

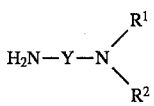

with Q, Y, $R^1$, $R^2$, m and n being the same as defined above for Formula (I), in a condensation reaction.

The present invention also relates to the use of the compounds corresponding to Formula (I) as catalysts, optionally incorporable catalysts, for the isocyanate addition reaction in the production of polyurethane foams by the isocyanate polyaddition process. These compounds are particularly useful as catalysts in the production of composite materials by backfoaming of plastic films with a reaction mixture which forms a polyurethane foam.

The variables Q, Y, $R^1$, $R^2$, m and n both above and in the following disclosure have the meanings already defined. The preferred meanings of these variables are as follows:

Q preferably represents the residue obtained by removal of the hydroxyl groups from a 2- to 6-functional alcohol having a molecular weight of from about 62 to about 4,000; more preferably, the residue obtained by removal of the hydroxyl groups from a difunctional to hexafunctional polyether polyol having a molecular weight of from about 200 to about 2,000 (most preferably from about 250 to about 1,000);

Y preferably represents an ethylene, 1,2-propylene or trimethylene group;

$R^1$ and $R^2$ preferably represent the same $C_{1-3}$ alkyl radicals or, together with the nitrogen atom and optionally an oxygen atom or another $C_{1-3}$ alkyl-substituted nitrogen atom, form a saturated heterocyclic 6-membered ring;

m preferably represents a whole number (on a statistical average) from 0 to 5 and n represents (on a statistical average) a number from 1 to 6, with the sum m+n being a number of from 1 to 6.

Particularly preferred compounds represented by Formula (I) are those which have (on a statistical average) less than 0.2 (preferably 0) or more than 1.8 (preferably at least 2) hydroxyl groups in the molecule so that the compounds do not act as chain terminators when used in the isocyanate addition reaction.

To prepare the acetoacetic acid esters of Formula (II) present in keto and enol form, alcohols corresponding to Formula (IV):

$$Q(OH)_{m+n} \quad (IV)$$

may be reacted with acetoacetic acid alkyl esters in a transesterification reaction at temperatures of from about 60° to about 210° C. (preferably at temperatures of from about 80° to about 160° C.) with removal by distillation of the alcohol component of the acetoacetic acid alkyl ester.

The acetoacetic acid alkyl esters may be used in less than or more than the equivalent quantity, based on the hydroxyl equivalents present. Thus, to obtain a complete conversion of the hydroxyl groups, it may be advisable or necessary to use an excess of acetoacetic acid alkyl ester. Use of less than the equivalent quantity of acetoacetic acid alkyl ester results in the formation of compounds which still contain free hydroxyl groups and which are therefore incorporable in the context of urethane chemistry. The reaction is preferably carried out in the absence of a solvent, although the use of solvents may be appropriate or necessary in certain cases (e.g., where poorly soluble hydroxyl compounds are used). When a solvent is used, suitable solvents are those which do not react with the reaction components and which have a sufficiently high boiling point that they may be separated from the alcohol component of the acetoacetic acid alkyl ester by distillation. Examples of suitable solvents include: hydrocarbons such as toluene or xylene; halogenated hydrocarbons such as chlorobenzene or dichlorobenzene; ethers such as ethylene glycol dimethyl ether, diethylene glycol dimethyl ether, diphenyl ether and dioxane; and amides such as dimethyl formamide, dimethyl acetamide or N-methyl pyrrolidone. In some cases, the addition of esterification catalysts such as dibutyl tin oxide, tin dichloride or tetrabutyl titanate may be advantageous but it is preferred that no catalyst be added.

In general, the reaction components are reacted under the described reaction conditions until distillation of the alcohol component of the acetoacetic acid alkyl ester used is complete or until the theoretically expected OH value is reached. To this end, it is of advantage or, in some cases, necessary to apply vacuum, particularly towards the end of the reaction.

Suitable alcohols (IV) include: 1- to 8- and preferably 2- to 6-functional low molecular weight alcohols with molecular weights in the range of from about 32 to about 399. Specific examples of such alcohols include: methanol, ethanol, n-propanol, the isomeric butanols, pentanols, hexanols, octanols, dodecanols, stearyl alcohol, ethylene glycol, propylene glycol, the isomeric butanediols, hexanediols, octanediols, glycerol, trimethylolpropane, pentaerythritol, sorbitol, sucrose and low molecular weight alkoxylation products of such alcohols having molecular weights in the range mentioned above.

Other suitable alcohols include: the polyacetals, polythioethers, polycarbonates, polyamides, polysiloxanes, polyesters, polylactones and, in particular, polyethers known from polyurethane chemistry which contain from 2 to 8 (preferably from 2 to 6) hydroxyl groups and have a molecular weight in the range of from about 400 to about 6,000, preferably in the range of from about 400 to about 4,000 and more preferably in the range of from about 400 to about 3,000.

In a particularly preferred embodiment, the alcohols (IV) are (m+n)-functional polyether polyols having molecular weights of from about 200 to about 2,000, preferably in the range of from about 250 to about 1,000. All molecular weights of the polyols (IV) disclosed herein are calculated on the basis of hydroxyl functionality and hydroxyl group content.

Mixtures of the monofunctional and polyfunctional alcohols (IV) may also be used for the production of the acetoacetic acid esters used as starting materials in the process of the present invention. The molecular weight of the alcohols (IV) given above are the (average) molecular weight calculated from the hydroxyl functionality and hydroxyl group content.

Suitable acetoacetic acid alkyl esters which may be reacted with the alcohols (IV) in a transesterification reaction include the $C_{1-6}$ alkyl esters of acetoacetic acid such as methyl, ethyl, n-propyl, n-butyl, tert.-butyl and n-hexyl acetoacetate. Methyl, ethyl and tert.-butyl acetoacetate are particularly preferred.

Primary/tertiary diamines (III) suitable for use in the process of the present invention are those for which Y, $R^1$ and $R^2$ are as defined above, particularly those having the preferred meanings defined above. Examples of suitable diamines include: 1-(dimethylamino)-3-aminopropane, 1-(diethylamino)-3-aminopropane, 1-(di-n-propylamino)-3-aminopropane, 1-(dimethylamino)-2-methyl-3-aminopropane, 1-(dimethylamino)-4-aminobutane or-5-aminopentane, N-(2-aminoethyl)-morpholine, N-(3-aminopropyl)-morpholine, N-(2-aminoethyl)-piperidine, N-(3-aminopropyl)-piperidine and N-(3-aminopropyl)-N'-n-propyl piperazine. In principle, it is also possible to use mixtures of such compounds. 1-(Dimethylamino)-3-aminopropane is preferably used as the primary/tertiary diamine (III).

The diamines (III) mentioned by way of example are known and, in some cases, are commercially obtainable.

To carry out the process of the present invention, the acetoacetic acid esters (II) are condensed with the primary/tertiary diamines (III) at temperatures of from about 10° to about 150° C. and preferably at temperatures of from about 20° to about 120° C. to form the aminocrotonic acid esters (I). It is preferred that water be removed by distillation from the reaction mixture during or subsequent to the reaction. The quantity in which the amine (III) is used is preferably gauged so that from about 0.8 to about 1.0 mol of primary amino groups is available for each equivalent of acetoacetate. In exceptional cases, for example where the reaction products are required to have a low viscosity, the diamines (III) may be used in a quantity of less than about 0.8 mol amino groups per mol acetoacetate groups. By contrast, the use of an excess of amine is less preferred because only equimolar quantities of amine are consumed. The excess quantity of amine component is then present in free form in the end product and must either be left in the product or removed (for example by distillation).

The reaction of amine (III) with acetoacetic acid ester (II) is preferably carried out in the absence of a solvent. However, it may be advisable or necessary n some cases to use solvents. Solvents may be used, for example, when the reactants are not sufficiently compatible or when the viscosity of the reaction mixture is too high. In cases such as these, it is best to use solvents which do not react with the reaction components and which can be readily removed (e.g., by distillation) from the reaction mixture on completion of the reaction. Solvents which form an azeotrope with water and which therefore facilitate removal of the water of reaction formed (for example, by boiling on a water separator) are particularly suitable. Examples of suitable solvents include: hydrocarbons such as toluene or xylene; halogenated hydrocarbons such as methylene chloride, chlorobenzene or dichlorobenzene; ethers such as ethylene glycol dimethyl ether, diethylene glycol dimethyl ether, diphenyl ether, tetrahydrofuran and dioxane; and amides such as dimethyl formamide, dimethyl acetamide and N-methyl pyrrolidone.

In general, the reaction components are reacted under the above-described reaction conditions until the theoretically expected quantity of water has distilled off or until the acetoacetate carboxyl band at 1740 cm$^{-1}$ in the IR spectrum of the reaction mixture has disappeared. The disappearance of the acetoacetate carboxyl band indicates complete conversion of the acetoacetate groups. It is generally advantageous and in some cases it may be necessary to apply vacuum to the reaction mixture to remove final traces of water, particularly towards the end of the reaction.

If the reactants are used in equivalent quantities (1 mol primary amino groups for each equivalent of acetoacetate) in the practical application of the process according to the invention, tertiary amines corresponding to Formula (I) which are substantially free from secondary products are formed. Where an excess of acetoacetic acid ester (II) is used, a mixture of compounds corresponding to Formula (I) and small quantities of secondary products are obtained. These secondary products are unreacted starting materials (II) and/or reaction products containing both unreacted acetyl acetic acid groups and structural units corresponding to the following formula (V):

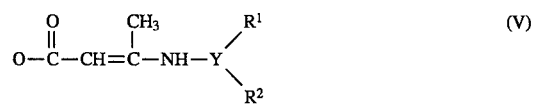

Even in these mixtures, however, compounds corresponding to Formula (I) containing tertiary amino groups form the principal component. The suitability of the mixtures for use as catalysts in accordance with the present invention is not significantly affected by the presence of the secondary products mentioned.

The compounds corresponding to Formula (I) containing tertiary amino groups of the present invention and mixtures thereof with the secondary products mentioned are substantially odorless. By suitable choice of the starting materials, particularly the alcohols (IV) on which the compounds of the present invention are based, compounds characterized by excellent compatibility with the polyether polyols typically used in polyurethane chemistry are obtained as the products of the process of the present invention. This is particularly true with respect to those compounds which are based on polyether polyols (IV) of the type previously described.

The compounds of the present invention are generally employed in quantities of from about 1 to about 20% by weight, based on the entire reaction mixture to catalyze the polyurethane foam forming reaction. In general, the compounds of the present invention are auxiliary agents which are used in addition to the typical polyhydroxyl compounds (particularly polyether polyols) and optionally in addition to the water used. However, in some cases, particularly where the compounds of the present invention are based on relatively high molecular weight alcohols (IV) the compounds of the present invention may also be used as the sole reactive component (aside from any water used) for the organic polyisocyanate(s).

In general, the compounds of the present invention are employed in quantities such that the reaction mixture contains from about 0.01 to about 1% by weight tertiary nitrogen atoms from the compound(s) of the present invention.

Those compounds corresponding to Formula (I) which contain hardly any or at least two hydroxyl groups per molecule are preferred as catalysts in the production of polyurethanes by the polyisocyanate addition process.

In addition to use as catalysts in the polyisocyanate addition process, the compounds of the present invention may also be used as surface-active agents (even in the form of their ammonium salts), emulsifiers or stabilizers.

Having thus described our invention, the following Examples are given as being illustrative thereof. All percentages given in these Examples are percentages by weight.

EXAMPLES

EXAMPLE 1

1a) Acetoacetylation 1000 g (9.80 OH equivalents) of a polyethertriol (OH value 102) prepared from trimethylolpropane and propylene oxide and 610 g (3.68 mol) of tert.butyl acetoacetate were heated to about 105° C. at 250 mbar. The distillation of tert.butanol began. The sump temperature was gradually increased to 130° C. commensurate with the distillation rate. When the distillation at 250 mbar/130° C. came to a stop, the pressure was reduced in stages to 20 mbar. The reaction mixture was then stirred for 2 hours in an oil pump vacuum (0.5 mbar).

The resulting product had a carbonyl value (CO value), as determined by titration with tetrabutyl ammonium hydroxide, of 153. The carbonyl value (CO value) indicates the number of keto-CO groups in mg per g substance. In the present case, both the keto form and the enol form were included in the titration. Accordingly, 36% of the hydroxyl groups initially present in the reaction mixture were converted.

1b) Amination 135 g (1.33 mol) of 1-(dimethylamino)-3-aminopropane were added dropwise over a period of 30 minutes at 25° C. to 500 g (1.36 CO equivalents) of the product of Example 1a). An internal temperature of 40° to 50° C. was maintained by gentle cooling with water. After exothermic reaction had abated, the reaction mixture was allowed to cool to around 30° C. and a water pump vacuum was gradually applied while heating to 50° C. Distillation of the water of reaction began. After the most of the water had been distilled off, the reaction mixture was stirred at 80° C./20 mbar until the water content was <0.1%. The clear yellowish product had a tert.amine nitrogen content of 3.1% and a viscosity of 3970 mPa.s/25° C.

EXAMPLE 2

500 g (1.36 CO equivalents) of the product of Example 1 a) and 191.5 g (1.33 mol) N-(3-aminopropyl)-morpholine were reacted as in Example 1b). The clear yellowish product had a tert.amine nitrogen content of 2.8% and a viscosity of 1120 mPa.s/25° C.

EXAMPLE 3

3a) Acetoacetylation 4900 g (21.88 OH equivalents) of a polyethertriol having an OH value of 250 which had been prepared from glycerol and propylene oxide and 2419 g (15.29 mol) tert.butyl acetoacetate were reacted as in Example 1a). The resulting product had a CO value of 117.6. 57% of hydroxyl groups initially present in the reaction mixture were converted.

3b) Amination 800 g (1.68 CO equivalents) of the product of Example 3a) and 171 g (1.68 mol) of 1-(dimethylamino)-3-aminopropane were reacted as in Example 1b). The clear yellowish product had a tert.amine nitrogen content of 2.5% and a viscosity of 1300 mPa.s/25° C.

EXAMPLE 4

4a) Acetoacetylation 4000 g (17.86 OH equivalents) of a polyethertriol having an OH value of 250 which had been prepared by propoxylation of trimethylopropane and subsequent ethoxylation of the propoxylation product (PO:EO ratio by weight= 1.1:98.9) and 3668 g (23.2 mol) of tert.butyl acetoacetate were reacted as in Example 1a). The resulting product was freed from excess t-butyl acetate by distillation. The product had a CO value of 178.5. 97.3% of the hydroxyl groups initially present in the reaction mixture were converted.

4b) Amination 471 g (1.5 CO equivalents) of the product of Example 4a) and 152 g (1.5 mol) 1-(dimethylamino)-3-aminopropane were reacted as in Example 1b). The clear yellowish product had a tert.-amine nitrogen content of 3.5% and a viscosity of 1070 mPa.s/25° C.

EXAMPLE 5

5a) Acetoacetylation 1000 g (3.3 equivalents) of a dimethyl polysiloxanediol with an OH value of 198 and 669 g (4.24 mol) tert.butyl acetoacetate were reacted as in Example 1a). The resulting product was freed from excess t-butyl acetate by distillation. This product had a CO value of 140.5. 80.8% of the hydroxyl groups initially present in the reaction mixture were converted.

5b) Amination 800 g (2.0 CO equivalents) of the product of Example 5a) and 204 g (2.0 mol) 1-(dimethylamino)-3-aminopropane were reacted as in Example 1b). The clear yellowish product had a tert.amine nitrogen content of 2.9% and a viscosity of 50 mPa.s/25° C.

EXAMPLE 6

6a) Acetoacetylation 1007 g (8.06 OH equivalents) of a polyether hexanol having an OH value of 450 which had been prepared from sorbitol and propylene oxide and 1654 g (10.47 mol) of tert.butyl acetoacetate were reacted as in Example 1a). The reaction mixture was freed from excess t-butyl acetate by distillation. 92% of the hydroxyl groups initially present in the reaction mixture were converted.

6b) Amination 500 g (2.28 CO equivalents) of the product of Example 6a) and 116 g (1.14 mol) 1-(dimethylamino)-3-aminopropane were reacted as in Example 1b). The clear light brown product had a tert, amine nitrogen content of 2.7% and a viscosity of 13,060 mPa.s/25° C.

EXAMPLE 7

7a) Acetoacetylation 1808 g (2.0 OH equivalents) of a monofunctional polyether having an OH value of 62 which had been prepared from butanol and ethylene oxide and 474 g (3.0 mol) tert. butyl acetoacetate were reacted as in Example 1a). The resulting product was freed from excess t-butyl acetate by distillation. The product had a CO value of 53.6. 94% of the hydroxyl groups initially present in the reaction mixture were converted.

7b) Amination 500 g (0.48 CO equivalent) of the product of Example 7a) and 48.8 g (0.48 mol) 1-(dimethylamino)-3-aminopropane were reacted as in Example 1b). The crystalline pale yellowish product had a tert.amine nitrogen content of 1.2%.

EXAMPLE 8

8a) Acetoacetylation 5000 g (5.0 OH equivalents) of a polyetherdiol having an OH value of 56 which had been prepared from propylene glycol and propylene oxide and 1028 g (6.5 mol) tert.butyl acetoacetate were reacted as in Example 1a). The resulting product was freed from excess butyl acetate by distillation. This product had a CO value of 51.98.4% of the hydroxyl groups initially present in the reaction mixture were converted.

8b) Amination 600 g (0.55 CO equivalent) of the product of Example 8a) and 77 g (0.54 mol) N-(3-aminopropyl)-piperidine were reacted as in Example 1b). The clear yellowish product had an amine nitrogen content of 1.1% and a viscosity of 1010 mPa.s/25° C.

Use Examples

Polyol formulation

In five parallel tests, 80 parts by weight of a polyether polyol having an OH value of 28 which had been prepared by propoxylation of trimethylolpropane and subsequent ethoxylation of the propoxylation product (PO:EO ratio by weight=82.5:17.5) and 20 parts by weight of a similarly prepared polyether polyol (OH value 28) grafted with 20% styrene/acrylonitrile (4:6) were mixed with the quantity of catalyst or activator shown in Table 1. 2.0 parts by weight of water were added as blowing agent in each test.

Polyisocyanate component

A polyisocyanate mixture of the diphenyl methane series (mixture of diisocyanatodiphenyl methane isomers and higher homologs thereof) having a viscosity (at 23° C.) of 200 mPa.s and an NCO content of 32% by weight was used in each of the following Examples.

Production of foams

The foams were produced by the hand foaming method. To this end, all of the components except for the polyisocyanate component were initially stirred for 30 seconds (stirring speed: 1000 r.p.m.). The polyisocyanate component was then added, followed by stirring for another 10 seconds at room temperature. In each of the Examples, the mixing ratio was 100:42, corresponding to an isocyanate index of 120.

The reactivity of the polyol component was determined in parallel tests through the cream time, the rise time and the gel time. As described above, the polyol formulation was combined with the polyisocyanate component with stirring in a glass beaker at room temperature. The cream time is the time which elapsed from the addition of the isocyanate to the beginning of the foaming reaction. The rise time is the time which elapsed from the addition of the polyisocyanate to the end of the foaming reaction. The gel time is the time which elapsed from the addition of the polyisocyanate to the tack-free state of the foam.

TABLE 1

| Activator used | From Example 1 | From Example 3 | From Example 4 | Comparison 1 | Comparison 2 |
|---|---|---|---|---|---|
| Quantity of activator (parts by weight) | 4.0 | 10.0 | 4.0 | 11.0 | 10.0 |
| Cream time(s) | 32 | 18 | 24 | 38 | n.d.* (>6.0) |
| Rise time(s) | 180 | 121 | 120 | 205 | n.d (>600) |
| Gel time(s) | 195 | 130 | 145 | 240 | n.d.* (>600) |

*n.d. = Not determined (the reaction times corresponded to the reaction time of a non-activated reaction mixture)

As can be seen from Table 1, the activators prepared in Examples 1, 3 and 4 (according to the invention) were compared with known polyether polyols containing tertiary amino groups. The activator of Comparison Example 1 was a polyether polyol containing tertiary amino groups and having an OH value of 500 which had been prepared by propoxylation of triethanolamine. The activator used in Comparison Example 2 was a polyether polyol containing tertiary amino groups having an OH value of 60 which had been prepared by propoxylation of ethylenediamine.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound containing a tertiary amino group which corresponds to the following Formula (I):

$$(HO)_mQ\left(-O-\overset{O}{\underset{\|}{C}}-CH=\overset{CH_3}{\underset{|}{C}}-NH-Y-N\overset{R^1}{\underset{R^2}{\diagdown}}\right)_n \quad (I)$$

in which
  Q represents a residue obtained by removal of one or more hydroxyl groups from an (m+n)-functional alcohol having a molecular weight of from about 106 to about 6,000,
  Y represents a difunctional aliphatic hydrocarbon radical containing from 2 to 6 carbon atoms with at least two carbon atoms being arranged between the two nitrogen atoms,
  $R^1$ and $R^2$ which may be the same or different, each represents an alkyl radical which radicals may together with the nitrogen atom and, optionally, other optionally alkyl-substituted hetero atoms form a saturated heterocyclic ring,
  m represents a number from 0 to 7 and
  n represents a number from 1 to 8,
with the proviso that the sum m+n is a number from 1 to 8.

2. The compound of claim 1 in which:
  Q represents a residue obtained by removal of hydroxyl groups from a 2- to 6-functional alcohol having a molecular weight of from about 106 to about 4,000,
  Y represents an ethylene, 1,2-propylene or trimethylene group,
  $R^1$ and $R^2$ each represent the same $C_{1-3}$ alkyl radical or together with the nitrogen atom and optionally, an oxygen atom, form a saturated heterocyclic 6-membered ring,
  m represents a number from 0 to 5 and
  n represents a number from 1 to 6, with the proviso that the sum m+n is a number from 2 to 6.

3. A process for the production of the compound containing tertiary amino groups of claim 1 comprising condensing compounds corresponding to the following Formula (II):

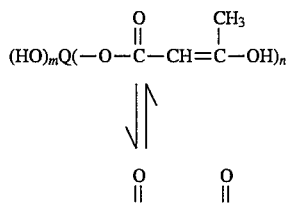

in which
- Q represents a residue obtained by removal of hydroxyl groups(s) from an (m+n)-functional alcohol having a molecular weight of from about 32 to about 6000,
- m represents a number from 0 to 7,
- n represents a number from 1 to 8, with the sum m+n being a number from 1 to 8, with compounds corresponding to the following Formula (III):

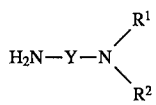

in which
- Y represents a difunctional aliphatic hydrocarbon radical containing from 2 to 6 carbon atoms with at least two carbon atoms being arranged between the two nitrogen atoms,
- $R^1$ and $R^2$ each represents an alkyl radical which radicals together with the nitrogen atom, and optionally, other optionally alkyl-substituted hetero atoms, may be attached to form a saturated heterocyclic ring.

4. The process of claim 3 in which
- Q represents a residue obtained by removal of hydroxyl groups from a 2- to 6-functional alcohol having a molecular weight of from about 106 to about 4,000,
- Y represents an ethylene, 1,2-propylene or trimethylene group,
- $R^1$ and $R^2$ each represent the same $C_{1-3}$ alkyl radical or are attached together with the nitrogen atom and optionally an oxygen atom to form a saturated heterocyclic 6-membered ring,
- m represents a number from 0 to 5, and
- n represents a number from 1 to 6, with the sum of m+n being a number from 2 to 6.

5. A process for the production of polyurethane foams comprising reacting
- (a) an organic polyisocyanate with
- (b) an isocyanate-reactive compound in the presence of
- (c) a catalyst containing a tertiary amino group which corresponds to the formula:

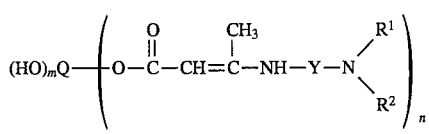

in which
- Q represents a residue obtained by removal of one or more hydroxyl groups from an (m+n)-functional alcohol having a molecular weight of from about 32 to about 6,000,
- Y represents a difunctional aliphatic hydrocarbon radical containing from 2 to 6 carbon atoms with at least two carbon atoms being arranged between the two nitrogen atoms,
- $R^1$ and $R^2$ which may be the same or different, each represents an alkyl radical which radicals may together with the nitrogen atom and, optionally, other optionally alkyl-substituted hetero atoms form a saturated heterocyclic ring,
- m represents a number from 0 to 7 and
- n represents a number from 1 to 8, with the proviso that the sum m+n is a number from 1 to 8.

6. A process for the production of composite materials from plastic films and polyurethane foam comprising backfoaming
- (1) a plastic film with
- (2) a reaction mixture comprising
  - (a) an organic polyisocyanate,
  - (b) an isocyanate-reactive compound and
  - (c) a catalyst containing a tertiary amino group which corresponds to the following formula:

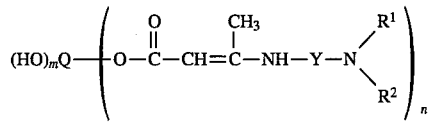

in which
- Q represents a residue obtained by removal of one or more hydroxyl groups from an (m+n)-functional alcohol having a molecular weight of from about 32 to about 6,000,
- Y represents a difunctional aliphatic hydrocarbon radical containing from 2 to 6 carbon atoms with at least two carbon atoms being arranged between the two nitrogen atoms,
- $R^1$ and $R^2$ which may be the same or different, each represents an alkyl radical which radicals may together with the nitrogen atom and, optionally, other optionally alkyl-substituted hetero atoms form a saturated heterocyclic ring,
- m represents a number from 0 to 7 and
- n represents a number from 1 to 8, with the proviso that the sum m+n is a number from 1 to 8.

* * * * *